United States Patent
Riad et al.

(10) Patent No.: US 12,251,577 B2
(45) Date of Patent: Mar. 18, 2025

(54) GEOMETRY-BASED REAL-TIME ADAPTIVE RADIOTHERAPY

(71) Applicant: Elekta AB (publ), Stockholm (SE)

(72) Inventors: Stella Lucie Riad, Sundbyberg (SE); David Andreas Tilly, Uppsala (SE); Peter Kimstrand, Uppsala (SE); Klas Marcks von Würtemberg, Stockholm (SE); Nina Terese Tilly, Uppsala (SE)

(73) Assignee: Elekta AB (publ), Stockholm (SE)

( * ) Notice: Subject to any disclaimer, the term of this patent is extended or adjusted under 35 U.S.C. 154(b) by 674 days.

(21) Appl. No.: 17/594,432

(22) PCT Filed: Sep. 30, 2019

(86) PCT No.: PCT/EP2019/076488
§ 371 (c)(1),
(2) Date: Oct. 15, 2021

(87) PCT Pub. No.: WO2021/001052
PCT Pub. Date: Jan. 7, 2021

(65) Prior Publication Data
US 2022/0176161 A1  Jun. 9, 2022

Related U.S. Application Data

(60) Provisional application No. 62/869,344, filed on Jul. 1, 2019.

(51) Int. Cl.
*A61N 5/10*   (2006.01)
*G06T 7/00*   (2017.01)
(Continued)

(52) U.S. Cl.
CPC ......... *A61N 5/1067* (2013.01); *A61N 5/1045* (2013.01); *A61N 5/1049* (2013.01);
(Continued)

(58) Field of Classification Search
CPC .. A61N 5/1067; A61N 5/1045; A61N 5/1049; A61N 2005/1087; A61N 5/107;
(Continued)

(56) References Cited

U.S. PATENT DOCUMENTS

| | | |
|---|---|---|
| 7,469,035 B2 | 12/2008 | Keall et al. |
| 9,652,871 B2 | 5/2017 | Han et al. |

(Continued)

FOREIGN PATENT DOCUMENTS

| | | |
|---|---|---|
| AU | 2019453270 | 2/2023 |
| CN | 101268476 | 9/2008 |

(Continued)

OTHER PUBLICATIONS

"Japanese Application Serial No. 2022-500018, Examiners Decision of Final Refusal mailed Jul. 11, 2023", W English Translation, 2 pgs.

(Continued)

*Primary Examiner* — Dhaval V Patel
(74) *Attorney, Agent, or Firm* — Schwegman Lundberg & Woessner, P.A.

(57) ABSTRACT

Techniques for adjusting radiotherapy treatment for a patient in real time are provided. The techniques include retrieving a reference plan that includes three-dimensional (3D) volume representation of information for the patient and a plurality of radiotherapy beam delivery segments; identifying a first portion of the 3D volume representation of information for a first beam delivery segment of the plurality of radiotherapy beam delivery segments that includes a volumetric portion of a target irradiated by the first beam delivery segment; accessing a deformation model representing patient deformation during a radiotherapy treatment fraction; deforming the first portion of the 3D volume representation of information based on the deformation (Continued)

model; and updating one or more parameters of a radiotherapy treatment device based on the deformed first portion of the 3D volume representation of information.

21 Claims, 5 Drawing Sheets

(51) Int. Cl.
*G06T 17/00* (2006.01)
*G16H 20/40* (2018.01)

(52) U.S. Cl.
CPC ............ *G06T 7/0016* (2013.01); *G06T 17/00* (2013.01); *G16H 20/40* (2018.01); *G06T 2207/30096* (2013.01); *G06T 2210/41* (2013.01)

(58) Field of Classification Search
CPC ..... A61N 5/1038; G06T 7/0016; G06T 17/00; G06T 2207/30096; G06T 2210/41; G16H 20/40
See application file for complete search history.

(56) References Cited

U.S. PATENT DOCUMENTS

| | | | |
|---|---|---|---|
| 2007/0041497 | A1* | 2/2007 | Schnarr .................. A61N 5/103 378/65 |
| 2008/0159478 | A1 | 7/2008 | Keall et al. |
| 2015/0306423 | A1* | 10/2015 | Bharat .................. A61B 8/4218 600/1 |
| 2016/0279444 | A1* | 9/2016 | Schlosser ............. A61N 5/1049 |
| 2018/0304099 | A1* | 10/2018 | Li ........................ A61B 5/0036 |

FOREIGN PATENT DOCUMENTS

| | | |
|---|---|---|
| CN | 104884126 | 9/2015 |
| CN | 114245752 | 3/2022 |
| JP | 2009502250 | 1/2009 |
| JP | 2015536783 | 12/2015 |
| WO | WO-2021001052 A1 | 1/2021 |

OTHER PUBLICATIONS

"Chinese Application Serial No. 201980099081.6, Office Action mailed Nov. 16, 2023", w English Translation, 16 pgs.

"International Application Serial No. PCT EP2019 076488, International Preliminary Report on Patentability mailed Jan. 13, 2022", 10 pgs.

"European Application Serial No. 19779895.2, Response to Communication pursuant to Rules 161 and 162 filed Aug. 15, 2022", 33 pgs.

"International Application Serial No. PCT/EP2019/076488, International Search Report mailed Nov. 27, 2019", 7 pgs.

"International Application Serial No. PCT/EP2019/076488, Written Opinion mailed Nov. 27, 2019", 10 pgs.

Ahunbay, Ergun E., et al., "An on-line replanning scheme for interfractional variations", Am. Assoc. Phys. Med. 35(8), Aug. 2008; 3607-3615, (Jul. 16, 2008), 9 pgs.

Cassioli, A., et al., "Aperture shape optimization for IMRT treatment planning", Phys. Med. Biol. 58 (2013) 301-318, (Dec. 21, 2012), 19 pgs.

Kamerling, Cornelis PH., et al., "Online dose reconstruction for tracked volumetric arc therapy: Real-time implementation and offline quality assurance for prostate SBRT", Medical Physics, 44(11), (Nov. 2017), 5997-6007.

Moore, Douglas, et al., "Fast leaf-fitting with generalized underdose/ overdose constraints for real-time MLC tracking", Med. Phys. 43 (1), Jan. 2016; 465-474, (Dec. 31, 2015), 10 pgs.

Wisotzky, Eric, et al., "Technical Note: A Novel Leaf Sequencing Optimization Algorithm which considers previous Underdose and Overdose Events for MLC Tracking Radiotherapy", (Oct. 15, 2015), 9 pgs.

"Australian Application Serial No. 2019453270, First Examination Report mailed Nov. 10, 2022", 3 pgs.

"Japanese Application Serial No. 2022-500018, Notification of Reasons for Refusal mailed Nov. 22, 2022", w English Translation, 7 pgs.

"Australian Application Serial No. 2019453270, Response filed Jan. 16, 2023 to First Examination Report mailed Nov. 10, 2022", 33 pgs.

"Chinese Application Serial No. 201980099081.6, Response filed Apr. 1, 2024 to Office Action mailed Nov. 16, 2023", W English Claims, 18 pgs.

"Chinese Application Serial No. 201980099081.6, Office Action mailed Apr. 27, 2024", w English translation, 10 pgs.

"Chinese Application Serial No. 201980099081.6, Response filed Jun. 18, 2024 to Office Action mailed Apr. 27, 2024", w current English claims, 39 pgs.

\* cited by examiner

GEOMETRY-BASED REAL-TIME ADAPTIVE RADIOTHERAPY

CLAIM FOR PRIORITY

This application is a U.S. National Stage Filing under 35 U.S.C. § 371 from International Application No. PCT/EP2019/076488, filed on Sep. 30, 2019, and published as WO2021/001052 on Jan. 7, 2021, which claims the benefit of priority of U.S. Application Ser. No. 62/869,344, filed Jul. 1, 2019; the benefit of priority of each of which is hereby claimed herein, and which applications and publication are hereby incorporated herein by reference in their entireties.

TECHNICAL FIELD

This disclosure relates generally to radiation therapy or radiotherapy. More specifically, this disclosure relates to systems and methods for adjusting parameters of a radiotherapy device during radiotherapy treatment.

BACKGROUND

Radiotherapy is used to treat cancers and other ailments in mammalian (e.g., human and animal) tissue. Radiotherapy include linear particle accelerator (LINAC)-based radiotherapy and circular particle accelerators (e.g., cyclotron, synchrotron, and synchrocyclotron). The direction and shape of the radiation beam should be accurately controlled to ensure a target tumour receives the prescribed radiation, and the placement of the beam should be such as to minimize damage to the surrounding healthy tissue including especially sensitive organs, often called the organ(s) at risk (OARs). Treatment planning can be used to control radiation beam parameters, and a radiotherapy device effectuates a treatment by delivering a spatially varying dose distribution to the patient according to a treatment plan.

OVERVIEW

In some embodiments, a computer-implemented method, transitory or non-transitory computer-readable medium, and a system comprising a memory and processor are provided for adjusting radiotherapy treatment for a patient in real time, the computer-implemented method, transitory or non-transitory computer-readable medium, and a system perform operations comprising: retrieving, by processor circuitry, a reference plan that includes three-dimensional (3D) volume representation of information for the patient and a plurality of radiotherapy beam delivery segments; identifying, by the processor circuitry, a first portion of the 3D volume representation of information for a first beam delivery segment of the plurality of radiotherapy beam delivery segments that includes a volumetric portion of a target irradiated by the first beam delivery segment; accessing, by the processor circuitry, a deformation model representing patient deformation during a radiotherapy treatment fraction; deforming, by the processor circuitry, the first portion of the 3D volume representation of information based on the deformation model; and updating, by the processor circuitry, one or more parameters of a radiotherapy treatment device based on the deformed first portion of the 3D volume representation of information.

In some implementations, the reference plan includes delineations of one or more of target volume(s) and/or one or more organs-at-risk (OARs), and wherein the 3D volume representation of information includes a plurality of two-dimensional image slices of the patient or a 3D volumetric representation of the patient.

In some implementations, the operations comprise generating the deformation model based on a description of the patient captured prior to or during the radiotherapy treatment fraction, the description being based on one or more image capture modalities.

In some implementations, the operations comprise generating a first 3D cut-out of the patient by projecting an opening of a collimator at the first beam delivery segment with respect to a source position; and identifying the first portion based on the first 3D cut-out of the patient.

In some implementations, the operations comprise generating a second 3D cut-out of the patient by projecting the opening of the collimator at a second of the plurality of radiotherapy beam delivery segments with respect to the source position; and identifying a second portion of the 3D volume representation of information for the second radiotherapy beam delivery segment based on the second 3D cut-out of the patient.

In some implementations, the volumetric portion in the first portion includes a part of the target to be irradiated and an organ-at-risk, and the operations further comprise: identifying a first set of voxels in the first portion that corresponds to the target to be irradiated; identifying a second set of voxels in the first portion that corresponds to the organ-at risk; deforming the first set of voxels separately from deforming the second set of voxels based on the deformation model; and changing a shape of the beam delivered during the first radiotherapy beam delivery segment based on the deformed first and second sets of voxels.

In some implementations, the operations comprise identifying a second portion of the 3D volume representation of information that includes a volumetric portion that is outside of a region that is irradiated in the first beam delivery segment.

In some implementations, the operations comprise deforming the first and second portions separately based on the deformation model; and updating the one or more parameters of the radiotherapy treatment device based on the deformed first and second portions.

In some implementations, deforming the first portion comprises applying a geometrical transform defined by the deformation model to the first portion.

In some implementations, the one or more parameters of the radiotherapy treatment device are updated based on treatment objectives defined by the reference plan, wherein at least one of the treatment objectives penalizes exposure of voxels belonging to an organ-at-risk (OAR) preventing adjustment of the one or more parameters that result in increased dose to the OAR.

In some implementations, the operations comprising updating the one or more parameters comprise adjusting positions of multi-leaf collimator leaves and jaws to fit an outline of an object depicted in the volumetric portion.

In some implementations, the operations comprise identifying a second portion of the 3D volume representation of information for a second of the plurality of radiotherapy beam delivery segments that includes a second volumetric portion of the target irradiated by the second beam delivery segment; deforming the second portion of the 3D volume representation of information based on the deformation model; and updating one or more parameters of the radiotherapy treatment device based on the deformed second portion of the 3D volume representation of information.

In some implementations, the operations comprise combining the first portion and the second portions into a combined portion of the 3D volume representation of information, wherein the deforming and updating is performed for the combined portion of the 3D volume representation of information.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
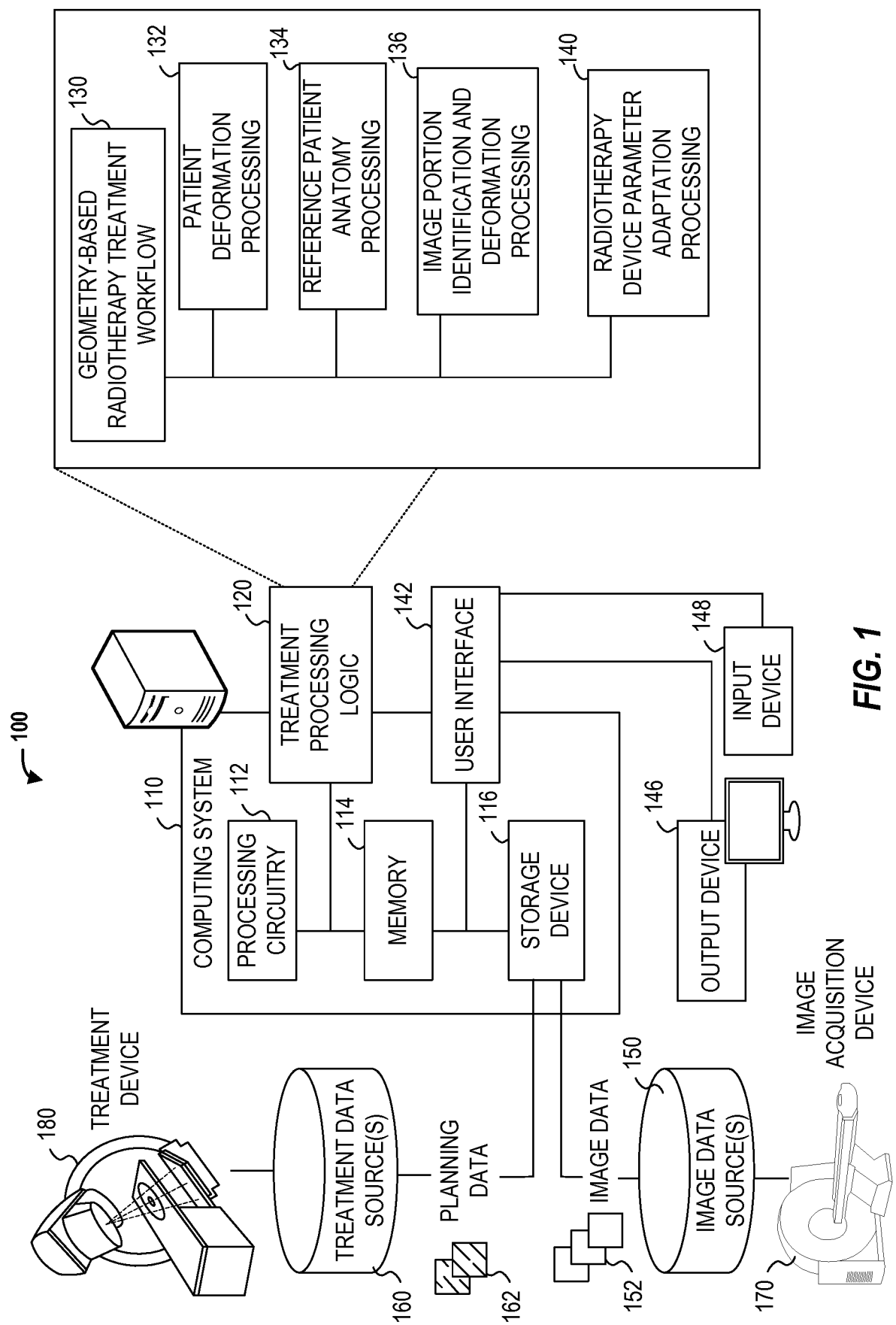
FIG. 1 illustrates an exemplary radiotherapy system adapted for performing geometry-based radiotherapy treatment according to some examples.

The present disclosure includes various techniques to improve and enhance radiotherapy treatment by adjusting radiotherapy device parameters (also referred to as "control points") in real time by considering individual object motion of one or more objects. The technical benefits include reduced exposure to radiation for normal tissue and more efficient treatment delivery. The disclosed techniques may be applicable to a variety of medical treatment and diagnostic settings or radiotherapy treatment equipment and devices.

Doses to vital organs and healthy tissue in radiotherapy treatments should be minimized due to the risk of serious injuries and late effects. However, treatment planning is normally performed prior to the patient's first treatment session, based on one or several image set/s of the patient (e.g., a snapshot in time of the patient). The treatment plan is then most often delivered in several fractions over a timespan of days to several weeks. A treatment plan consists of several beam segments of different weights—cumulative metersets—delivered at discrete or continuous gantry angles with different multi-leaf collimator and jaw settings shaping the fluence of the segments. For charged particles it is the cumulative metersets per spot and the speed of the scanning magnets that can be changed. Over the course of treatment, the patient will be approximated as static, ignoring any internal organ motion or change of shape during fractions as well as changes between fractions such as weight loss or tumour volume reduction. In order to compensate for these discrepancies, margins are applied to the target volume to ensure coverage and thus local control of the tumour. Particularly, to compensate for these discrepancies, a margin around a region to be irradiated by a radiotherapy beam is applied to increase the radiation exposure (e.g., increasing the size of the beam shape) in a given segment. While such an approach increases the likelihood that a tumour is irradiated with the prescribed dose in a given segment, the approach can have the negative consequence of overexposing an OAR and surrounding normal tissue to radiation.

The position and shape of tumours and sensitive organs in the surrounding tissue, called OARs, are not static but are affected by external forces, e.g., gravity, as well as internal motion, such as breathing, heartbeat, bowel movements, etc., and may thus move and change shape during each fraction of the treatment. In addition, the tumour and OARs may move in between fractions, due to, for example, the bladder filling or the patient losing weight, and furthermore the tumour may decrease in volume in between treatment fractions, as a result of the treatment. Therefore, there may be a discrepancy between planned dose and the actual delivered dose to both target and OAR. One way of minimizing this discrepancy is to actively track the target movement, and possibly the OARs, and adapt the current beam segment accordingly during delivery. The intention of tracking is to dynamically adapt the current segment (and possibly subsequent segments) in order to fulfil the intended dose distribution, calculated on the static patient. Tracking has the potential of reducing margins, thereby decreasing dose to surrounding normal tissue and OARs. For simple, well-defined, rigid patient deformations, such as translations and rotations, it is rather straightforward to adapt a given segment in order to achieve a dose distribution similar to the reference dose. However, in the general case, the patient deformation is not rigid and therefore it is significantly more difficult to reproduce the dose distribution.

Prior approaches adapt beam delivery segments during radiotherapy by considering movement of the entire target volume as a whole. Namely, prior approaches determine new segment parameters according to the projection of the entire deformed target. In this way, the prior approaches still end up over- or under-delivering radiation to the tumour and/or exceeding the dose allowed to an OAR. In order to optimize radiotherapy dose delivery to a target (e.g., a tumour) or reduce the amount of radiation delivered to an OAR, the disclosed techniques perform modifications to the radiotherapy device parameters by considering motion and deformation parts of objects (e.g., a region of interest, such as an OAR and/or target) visible in a beam's eye view and/or motion and deformation parts of objects not visible in a beam's eye view. Namely, the disclosed techniques modify radiotherapy treatment device parameters (e.g., control points) based only on the a stack of 2D images of a target volume that intersects a given segment (e.g., based on radiotherapy beam delivery parameters or control points for a given segment in a fraction), such as the stack of 2D images (from which a 3D representation can be reconstructed) that are in the beam's eye view, and movement of an object, a target to be irradiated (e.g., a tumour), and/or OAR in the stack of 2D images under consideration. In this way, the disclosed techniques reduce the amount of radiation to which an OAR is exposed and increase the amount of radiation delivered to a tumour in a given segment.

In some embodiments, in order to perform real-time adjustments to the radiotherapy device parameters based on patient geometry, the disclosed techniques retrieve, by processor circuitry, a reference plan that includes three-dimensional (3D) image information for a patient and a plurality of radiotherapy beam delivery segments. The disclosed embodiments identify, by the processor circuitry, a first portion of the 3D image information for a first beam delivery segment of the plurality of radiotherapy beam delivery segments that includes a volumetric portion of the target irradiated by the first beam delivery segment. The disclosed embodiments access, by the processor circuitry, a deformation model (e.g., movement model representing patient movement) during a radiotherapy treatment fraction and deform, by the processor circuitry, the first portion of the 3D image information based on the movement model. The disclosed embodiments update, by the processor circuitry, one or more parameters of the radiotherapy treatment device based on the deformed first portion of the 3D image information.

In particular, the disclosed techniques provide a process for tracking, which uses a patient deformation model and reference geometry of the region of interest of the patient at every instant during the treatment. In this process, sub-volume(s) of the target and/or OARs are determined by the intersection of the reference segment (e.g., the beam delivery segment parameters or control points specifying the positions of the MLC leaves and jaws, couch position, and/or other radiotherapy device parameters) with the reference geometry, then the current segment (e.g., one or more of the radiotherapy device parameters) is dynamically adapted according to the current patient deformation model. In some cases, the intersection of the reference segment and the reference geometry lies in the isocentre plane of the radiotherapy device. As input, the process receives an optimized treatment plan, referred to as the reference plan, and a geometrical transform (e.g., the patient deformation or movement model) describing the current deformation of the patient compared to the reference geometry at each instant in time. The optimized or initial reference plan is computed prior to the first treatment fraction, but then the reference plan could be updated sometime in between fractions either for each fraction, resulting in a plan-of-the-day, or at a longer interval. The plan may include delineations of target volume(s) (e.g., tumour(s)) and OAR(s), and the patient anatomy deformation updates may be provided by displacement vector fields.

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy dose calculations or radiotherapy machine configuration parameters.

Specifically, the following processing operations may be implemented as part of a geometry-based radiotherapy treatment workflow 130, implemented by treatment processing logic 120. It will be understood, however, that many variations and use cases of the following treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device, also referred to herein as a radiotherapy device), and treatment data source(s) 160. As an example, the radiotherapy processing computing system 110 can be configured to monitor current patient geometry to calculate dose delivery to a subject (e.g., from one or more MR images) within a given fraction in real time and modify parameters of the radiotherapy device for subsequent doses delivered in the same fraction based on a comparison of the calculated dose delivery to an expected dose delivery specified in a treatment plan by executing instructions or data from the treatment processing logic 120. Specifically, the radiotherapy processing computing system 110 can be configured to monitor current patient geometry to update and/or create a patient deformation model (e.g., patient movement model) to be used in deforming one or more portions of a 3D volume for a given beam delivery segment of a radiotherapy treatment plan. Once the portions are deformed, the radiotherapy processing computing system 110 can update one or more control points of the radiotherapy device to adapt the beam delivery segment (e.g., change the shape of the beam delivered in one or more segments).

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans (e.g., training data, treatment planning strategies, patient movement models, patient deformation models, beam delivery segment information, 3D and/or 2D image information for a patient, and device adjustment parameters, and the like), software programs (e.g., image processing software, image or anatomical visualization software, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry based) or software-based processor, for example, a multi-core design or a plurality of processors each having a multi-core design. The processing circuitry 112 can execute sequences of transitory or non-transitory computer program instructions, stored in memory 114, and accessed from the storage device 116, to perform various operations, processes, methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, ML technique parameters, device adaptation functions, data, or transitory or non-transitory computer-executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., CT and/or MR images), for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data 162 as a result of radiotherapy device parameter adjustments or segment adaptation generated by the geometry-based radiotherapy treatment workflow 130; the image data source 150 may also provide or host the image data 152 for use in the geometry-based radiotherapy treatment workflow 130.

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120.

In addition, the processing circuitry 112 may utilize software programs to generate intermediate data such as updated parameters to be used, for example, by a neural network model, machine learning model, geometry-based radiotherapy treatment workflow 130, or other aspects involved with generation of device parameter adjustments or segment adaptation, as discussed herein. Further, such software programs may utilize the treatment processing logic 120 to implement the geometry-based radiotherapy treatment workflow 130 to produce updated radiotherapy parameters to provide to the treatment data source 160 to modify a dose delivered to a target within a given fraction and/or for presentation on output device 146, using the techniques further discussed herein. The processing circuitry 112 may subsequently then transmit the updated radiotherapy parameters via a communication interface and the network to the treatment device 180, where the updated parameters will be used to treat a patient with radiation via the treatment device 180, consistent with results of the workflow 130. Other outputs and uses of the software programs and the workflow 130 may occur with use of the radiotherapy processing computing system 110. Radiotherapy parameters (also referred to as control points) may include, for each segment or portion of a given treatment fraction, MLC positions and settings, gantry angle, radiation dose amount (e.g., amount of monitor units (MU)), radiotherapy beam direction, radiation beam size, arc placement, beam on and off time duration, machine parameters, gantry speed, MRI pulse sequence, any combination thereof, and so forth.

In an example, the image data 152 may include one or more MRI images (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images) and the like. Further, the image data 152 may also include or be associated with medical image processing data, for instance, training images, and ground truth images, contoured images, and dose images. In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise an MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., an MRI device combined with a linear accelerator, also referred to as an "MRI-Linac"). Such an MRI-Linac can be used, for example, to determine a location of a target in the patient, so as to direct the radiation beam accurately according to the radiation therapy treatment plan to a predetermined target. For instance, a radiation therapy treatment plan may provide information about a particular radiation dose to be applied to each patient. The radiation therapy treatment plan may also include other radiotherapy information and radiotherapy device parameters, such as beam angles, dose-volume-histogram information, the number of radiation beams to be used during therapy, the dose per beam, and the like. The MRI-Linac can be used to compute, generate, and/or update a patient deformation model to deform image portions of a 3D or 2D image of a patient corresponding to a given beam delivery segment.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on and off time duration, machine parameters, segments, MLC configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, image portions that are identified and deformed for a given treatment segment, a target, localizing a target and/or tracking a target, or any related information to the user. The input device 148 connected to the user interface 142 may be a keyboard, a keypad, a touch screen or any type of device using which a user may input information to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system 100 may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumour or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumour. In an example, 2D slices can be determined from information such as a 3D CBCT or CT, or MRI volume. Such 2D slices can be acquired by the image acquisition device 170 in "near real-time" while a patient is undergoing radiation therapy treatment, for example, when using the treatment device 180 (with "near real-time" meaning acquiring the data without (or with minimal) lag between image acquisition and treatment, as known in the art). In an example, 3D volumetric representation of a region of interest can be generated using a stack of one or more 2D slices.

Figure 2:
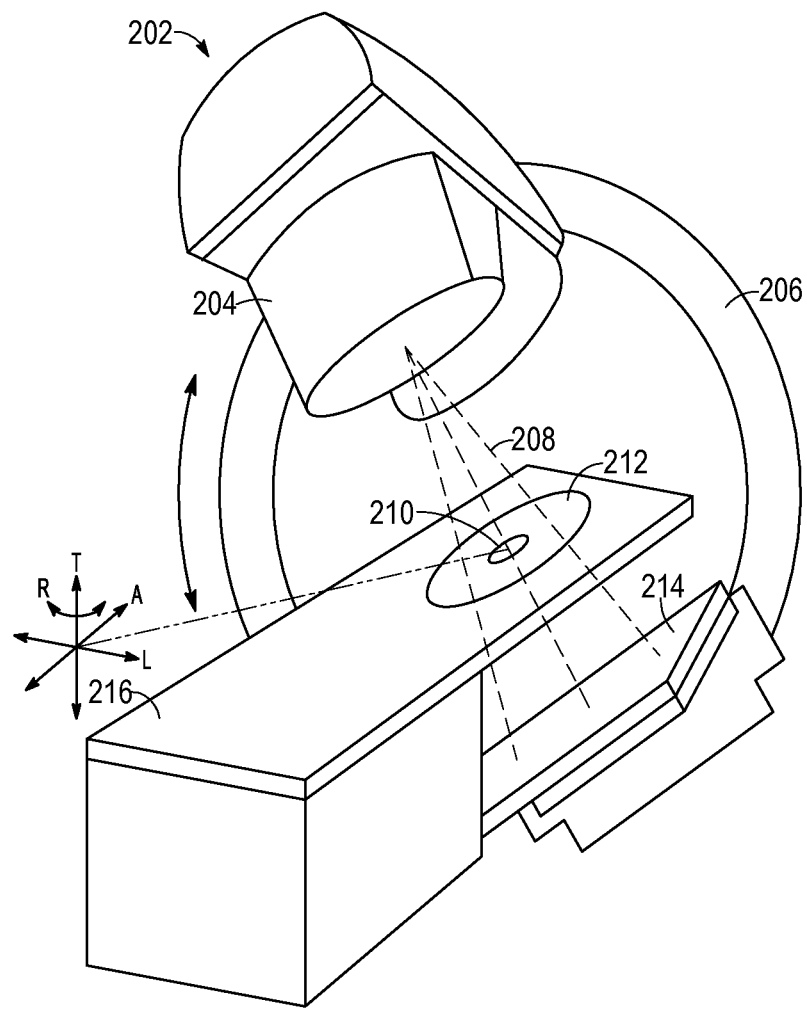
FIG. 2 illustrates an exemplary image-guided radiotherapy device according to some examples of the disclosure.

FIG. 2 illustrates an exemplary image-guided radiation therapy device 202 that includes a radiation source, such as an X-ray source or a linear accelerator, a couch 216, an imaging detector 214, and a radiation therapy output 204. The radiation therapy device 202 may be configured to emit a radiation therapy beam 208 to provide therapy to a patient. The radiation therapy output 204 can include one or more attenuators or collimators, such as a multi-leaf collimator (MLC).

As an example, a patient can be positioned in a region 212, supported by the treatment couch 216, to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, the gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation therapy beam 208 according to a radiation therapy treatment plan. Both the couch 216 and the gantry 206 are independently moveable from one another in multiple degrees of freedom, which allows the patient to be positioned such that the radiation therapy beam 208 can precisely target the tumour.

The coordinate system (including axes A, T, and L) can have an origin located at an isocenter 210. The isocenter 210 can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the radiation therapy beam 208. The imaging detector 214 can be mounted on the gantry 206, preferably opposite the radiation therapy output 204, such as to maintain alignment with the radiation therapy beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the therapy beam 208, or the imaging detector 214 can be used for imaging the patient's anatomy, such as portal imaging. The control circuitry of the radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the radiation therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient consistent with or according to a radiotherapy treatment plan and parameters of a device adjusted within a given fraction, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Referring back to FIG. 1, the geometry-based radiotherapy treatment workflow includes patient deformation processing 132, reference patient anatomy processing 134, image portion identification and deformation processing 136, and radiotherapy device parameter adaptation processing 140. In an implementation, the processes implemented by the reference patient anatomy processing 134, image portion identification and deformation processing 136, and the radiotherapy device parameter adaptation processing 140 may be performed in real time during a given treatment fraction (e.g., as each beam delivery segment begins or ends) and/or before or after a patient undergoes a given treatment fraction.

In an example, reference patient anatomy processing 134 obtains a radiotherapy treatment plan for a given patient. The radiotherapy treatment plan may be generated by a clinician for delivery of radiotherapy during one or more radiotherapy treatment fractions. The radiotherapy treatment plan includes image information for the patient representing OAR(s) and a target to be irradiated. The image information may be a collection of 2D or 3D MR or CT images. The radiotherapy treatment plan also includes a plurality of radiotherapy beam delivery segments. Each beam delivery segment defines a set of radiotherapy device control points that are used throughout the radiotherapy treatment fraction. Specifically, one beam delivery segment defines a first set of control points used during a first time point or time interval of the treatment fraction and a second beam delivery segment defines a second set of control points used during a second time point or time interval of the treatment fraction that is subsequent to, prior to, and/or adjacent to the first time point. The plurality of beam delivery segments define the beam delivery parameters that are used throughout the treatment fraction. The radiotherapy treatment plan also includes delineations of one or more of target volume(s) and/or one or more OAR(s).

In an example, patient deformation processing 132 generates, obtains, and/or updates a patient deformation model. The patient deformation model represents an estimate or predicted movement of the patient and/or regions of the patient during an upcoming, real-time, and/or past treatment fraction. In an embodiment, the patient deformation model is generated based on at least one of one or more descriptions of the patient captured prior to or during the radiotherapy treatment fraction. The one or more descriptions may be generated based on one or more magnetic resonance (MR) images, one or more computed tomography (CT) images, one or more cone beam computed tomography (CBCT) images, surface scanning, or radio beacons. The patient deformation model may represent actual and/or estimated (predicted) patient movement at particular times or time intervals during the treatment fraction and/or throughout the treatment fraction. The patient deformation model may be provided as one or more displacement vectors.

In an example, image portion identification and deformation processing 136 obtains control points for a given segment defined by the radiotherapy treatment plan. The image portion identification and deformation processing 136 processes the 3D or 2D image information in the reference treatment plan to identify a given portion of the 3D or 2D image information that intersects the given segment. Specifically, the image portion identification and deformation processing 136 identifies the portion of the 3D or 2D image information that is within the beam's eye view at a particular one of the beam delivery segments. The image portion identification and deformation processing 136 may identify one or more other portions for each additional segment that is in the treatment plan in the same manner.

In some implementations, for each segment of the reference plan, a whole or part of the target volume will be irradiated. The image portion identification and deformation processing 136 defines the identified portion as an elementary tracking volume (ETV) for the given segment, which is determined by the intersection of the three-dimensional target volume information (e.g., a moving target volume) and the three-dimensional cut-out of the patient, created by projecting the collimator opening of the segment with respect to the source position throughout the patient volume. Specifically, the portion that is identified in the reference patient image information includes the portion of the moving target volume that is irradiated by the current segment. The image portion identification and deformation processing 136 may compute or identify the portion of the patient volume that is irradiated or that is within a beam's eye view by tracing a path from an imaginary eye (the MLC view or beam's eye view) through each pixel in a virtual screen, and calculating the colour of the object visible through it. Any other tomographic reconstruction technique can be utilized to generate the projection images from the MLC beam's eye view of the anatomy depicted in the 3D images of the patient for a given beam delivery segment.

In this way, the image portion identification and deformation processing 136 only tracks or processes the part of the moving target volume that is within the collimator opening. Recreating dose to the ETV corresponds to the objective of ensuring target coverage. Given a voxelized representation of the patient, the set of selected voxels belonging to the ETV can formally be described by $\{v \in P: M*v \in S\}$ where P is the set of voxels in $\mathbb{R}^3$ belonging to the ETV, M is the homogenous transformation matrix that projects a point onto the isocentre plane with respect to the radiation source, and S is the set of points in $\mathbb{R}^2$ belonging to the isocentre plane that are limited by the isocentre projection of the collimator opening of the segment. In this manner, a tracking volume is created for each beam segment of the reference plan. Specifically, the image portion identification and deformation processing 136 may identify a portion of the patient images that is within the beam's eye view during a given segment and that only includes the region within the portion corresponding to the tumour (or target to be irradiated). Other regions (e.g., OAR(s)) that are also within the beam's eye view within the identified portion may be excluded. In some embodiments, the image portion identification and deformation processing 136 may identify first and second portions for a given segment. The first portion may include the region of the portion of the images within the beam's eye view that includes only the target and the second portion may include the region of the portion of the images within the beam's eye view that includes only the OAR(s). In this way, motion of the OAR and the tumour (or target) at each segment can be separately tracked and represented. In some embodiments, the identified portion includes all or a portion of the target to be irradiated during the treatment segment and all or a portion of the OAR that is within or outside of the beam's eye view during the treatment segment.

In some implementations, in addition to the ETV, the image portion identification and deformation processing 136 tracks or identifies, within the volume representation based on 3D or 2D reference patient images, one or more additional volumes. The additional image portions that are created can include a tracking volume that is the complement of the ETV, such as the voxels in the volume representation based on the 2D or 3D reference patient images that are not within the boundaries of the segment, defined by $\{v \in P: M^*v \notin S\}$. The objective corresponding to this volume is minimization of overdose in the target voxels. Specifically, the image portion identification and deformation processing 136 may identify for a given segment a first portion of the reference patient images that is within the beam's eye view and a second portion of the reference patient images that is not within the beam's eye view (e.g., the second portion may be a portion of the reference patient images that is within the beam's eye view at a second segment within the treatment fraction).

As another example, the image portion identification and deformation processing 136 includes OAR(s) among the tracking volumes for each beam segment of the reference plan. The image portion identification and deformation processing 136 can track both the part of the OAR(s) inside of the beam segment, such as $\{v \in O: M^*v \in S\}$, where O is the set of voxels in $\mathbb{R}^3$ belonging to an OAR, and the complement to this volume $\{v \in O: M^*v \notin S\}$. Similarly, healthy tissue structures can be introduced in the tracking volume, again possibly including both the part of the volume intersecting and the part not intersecting the current segment. Adding these volumes to the tracking volume will enforce plan objectives, related to overdose of these structures, to be met during tracking, for each beam segment. As described herein, a volume intersects a segment when the control points of the segment define a radiotherapy beam that irradiates a given portion (but not the entirety) of objects depicted or included in the 2D or 3D patient reference images.

For example, the image portion identification and deformation processing 136 may generate a first 3D cut-out of the patient by projecting an opening of a collimator at a first radiotherapy beam delivery segment with respect to a source position. The image portion identification and deformation processing 136 identifies a first portion of the reference patient imaging information that is within the beam's eye view for the given segment based on the 3D cut-out of the patient. The image portion identification and deformation processing 136 may generate a second 3D cut-out of the patient by projecting the opening of the collimator at a second of the plurality of radiotherapy beam delivery segments with respect to the source position. The image portion identification and deformation processing 136 may identify a second portion of the 3D image information that is within the beam's eye view during the second segment based on the second 3D cut-out of the patient.

In some embodiments, the image portion identification and deformation processing 136 obtains a patient deformation model from the patient deformation processing 132. The image portion identification and deformation processing 136 deforms or adjusts a position or orientation of the image portion(s) that is/are identified (e.g., the image portion of the reference images that is within the beam's eye view, that is outside of the beam's eye view during the given segment, that includes only the tumour within the beam's eye view during the given segment, that includes only the OAR within the beam's eye view during the given segment, that includes a portion of the OAR and a portion of the tumour within our outside the beam's eye view during the given segment, and/or any combination thereof) based on the patient deformation model. The image portion identification and deformation processing 136 performs such deformation and/or adjustments in real time during a treatment fraction, after a radiotherapy treatment fraction, and/or before a radiotherapy treatment fraction. In an embodiment, the image portion identification and deformation processing 136 performs such deformation and/or adjustments by applying a geometrical transform to image portion(s) at the given instant or segment of the radiotherapy fraction.

Figure 3:
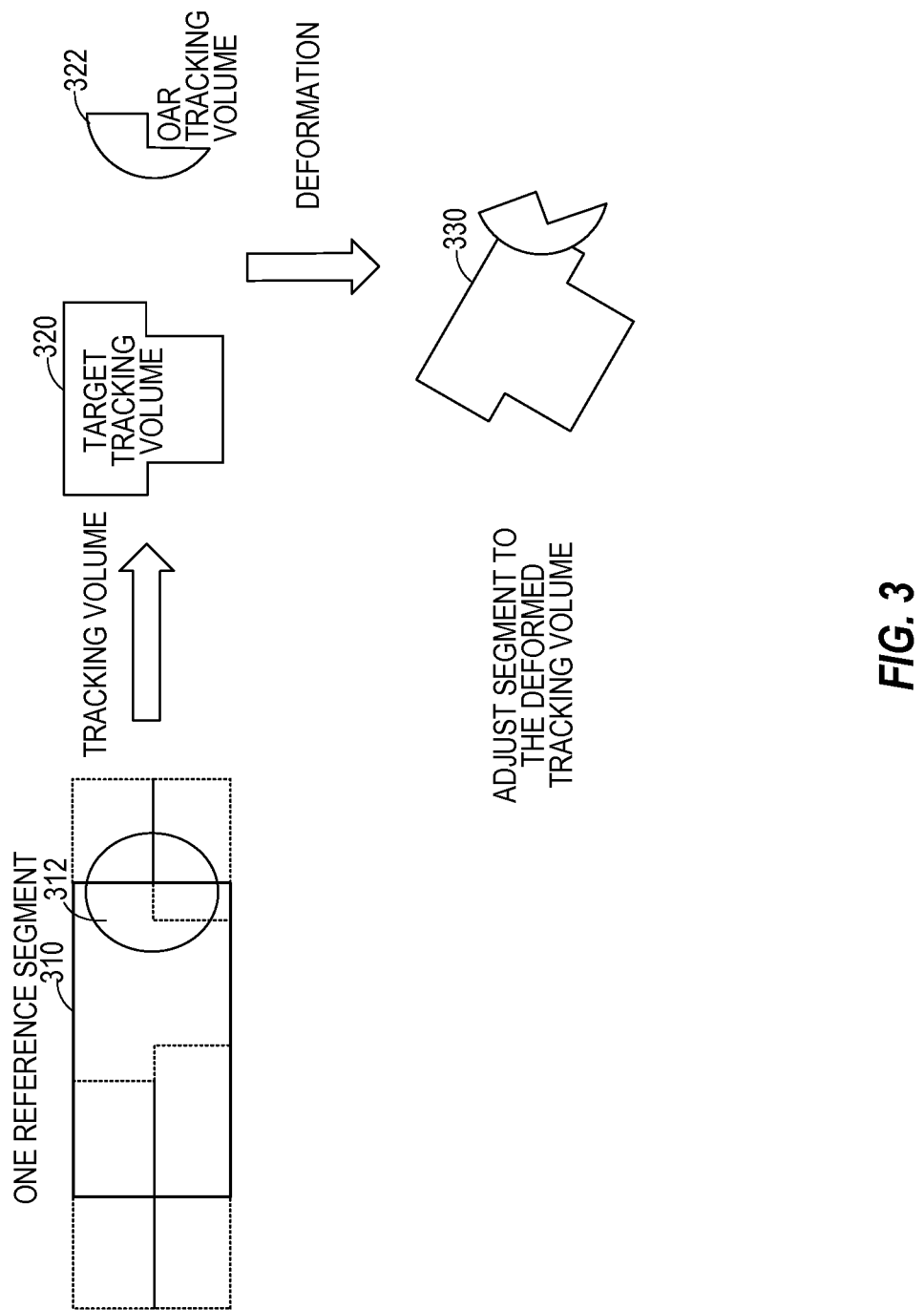
FIG. 3 illustrates exemplary radiotherapy treatment image deformation according to some examples of the disclosure.

FIG. 3 illustrates exemplary radiotherapy treatment image deformation according to some examples of the disclosure. For example, as shown in FIG. 3, image portion identification and deformation processing 136 obtains a reference segment 310 that dose to a portion of the patient volume specified in a patient's radiotherapy treatment plan. Specifically, the image portion identification and deformation processing 136 obtains the control points for a given segment and also obtains the corresponding 2D or 3D image information from the treatment plan. The image portion identification and deformation processing 136 projects a view of the collimator or MLC using the control points to identify a portion of the volume representation based on the 2D or 3D image information that is within view of the collimator or MLC during the given segment. This portion of the patient volume is irradiated during the delivery of the reference segment 310. FIG. 3 shows reference segment 310 and a projection of the 3D volumes onto a 2D plane.

For each reference segment 310, one or more regions (tracking volumes) are identified by the image portion identification and deformation processing 136. For example, the image portion identification and deformation processing 136 identifies a first region 320 that includes only the target or tumour that is in the reference segment 310. The first region 320 is drawn to include a portion 312 of the target that, in 3D, is in the reference segment 310 below the OAR in view from the collimator in the reference segment 310. Specifically, the image portion identification and deformation processing 136 identifies a first set of voxels in the reference segment 310 that correspond to a target to be irradiated. The image portion identification and deformation processing 136 identifies a second region 322 that only includes a portion of the OAR that is in the reference segment 310. Specifically, the image portion identification and deformation processing 136 identifies a second set of voxels in the reference segment 310 that correspond to an OAR that is within the beam's eye view and/or outside of the beam's eye view. In an embodiment, the image portion identification and deformation processing 136 may identify a third region (not shown) that includes both the OAR and the tumour or target that is in the reference segment 310 and/or that is part of another reference segment that is a complement to the reference segment 310 and/or not in the beam's eye view.

Once the tracking volumes are identified, the image portion identification and deformation processing 136 obtains a patient deformation model. Using the patient deformation model, the image portion identification and deformation processing 136 deforms (e.g., adjusts a shape, size, position, and/or orientation) each tracking volume separately and independently. For example, the image portion identification and deformation processing 136 deforms the first set of voxels separately from deforming the second set of voxels based on the deformation model. In this way, for example, the image portion identification and deformation processing 136 deforms the region of the reference segment 310 that includes only the target or tumour separately and independently from the region of the reference segment 310 that includes only the OAR. The image portion identification and deformation processing 136 generates a deformed tracking volume(s) 330 that represents the adjustments made to the portions of the patient volume included in the tracking volume(s). In some embodiments, the image portion identification and deformation processing 136 combines the first and second regions 320/322 into a single deformed tracking volume 330. In some cases, when setting leaves of the MLC, the first region 320 that includes only the tumour is considered separately from the second region 322 that includes only the OAR. In some embodiments, the image portion identification and deformation processing 136 stores the deformed versions of the first and second regions 320/322 as separate images. Specifically, as one example, as shown, based on the deformation model, the image portion identification and deformation processing 136 determines that the target included in the first region 320 has rotated 20 degrees clockwise relative to its position in the reference segment 310. Also, based on the deformation model, the image portion identification and deformation processing 136 determines that the OAR in the second region 322 has rotated 10 degrees counter-clockwise. The image portion identification and deformation processing 136 generates the deformed tracking volume(s) 330 that include or take into account these deformations of the first and second regions 322. In a similar manner, any other tracking volume or region that is identified for the current segment and/or one or more subsequent or previous segments (adjacent or non-adjacent) can be similarly deformed based on the deformation model. In some embodiments, the image portion identification and deformation processing 136 repeats the process of generating the deformed tracking volume(s) 330 one or more times for every segment in the treatment plan for a given treatment fraction. In some embodiments, the image portion identification and deformation processing 136 is performed once for a given segment to define the image portion and deformation of the image portion is performed more than once for a remaining set of segments.

Referring back to FIG. 1, the radiotherapy device parameter adaptation processing 140 computes new control points or updates the control points for a given segment based on the deformed identified portion (e.g., deformed tracking volume(s) 330) provided by the image portion identification and deformation processing 136. Specifically, the radiotherapy device parameter adaptation processing 140 changes a shape of the beam delivered during the beam segment for which the deformation was computed or determined based on the deformed first and second sets of voxels (FIG. 3) (e.g., the first set of voxels in the reference segment 310 that correspond to a target to be irradiated and the second set of voxels in the reference segment 310 that correspond to an OAR that is within the beam's eye view and/or outside of the beam's eye view). As one example, the radiotherapy device parameter adaptation processing 140 computes or updates one or more parameters of the radiotherapy treatment device based on treatment objectives defined by the reference plan, in which at least one of the treatment objectives penalizes exposure of voxels belonging to an organ-at-risk (OAR) preventing adjustment of the one or more parameters that result in increased dose to the OAR. In some embodiments, the radiotherapy device parameter adaptation processing 140 updates the one or more parameters (e.g., adjusts positions of multi-leaf collimator leaves and jaws) to fit an outline of an object (e.g., a target or tumour) depicted in the volumetric portion of the reference images of the given segment. Specifically, the radiotherapy device parameter adaptation processing 140 identifies a beam segment in the treatment plan corresponding to the deformed identified portion.

Namely, the radiotherapy device parameter adaptation processing 140 determines which beam segment was used to identify the portion that is within the beam's eye view during the beam segment. Then, the radiotherapy device parameter adaptation processing 140 obtains the control points (e.g., the radiotherapy device parameters) specified by the identified beam segment. Once the control points are obtained, the radiotherapy device parameter adaptation processing 140 adjusts one or more of the control points based on the deformation (e.g., the change in shape, orientation, and/or position) of the portion that depicts the object (e.g., the OAR and/or the tumour). In an embodiment, the control points are adjusted to increase, decrease, or change the shape of the radiotherapy beam that is delivered during the identified segment to increase or decrease the amount of radiation exposure to the target and/or the OAR.

In an embodiment, based on the deformed tracking volume(s) (e.g., the identified portion that includes an object that is within the beam's eye view during a segment), the new segment (e.g., new control points) is determined by geometrically trying to recreate the intent of the reference segment. The updated segment can be created in several different ways, depending on what objective of the reference plan is deemed most important. Due to the limited resolution of both the MLC leaves, which ought to be adapted to the projection, and, if voxelized, possibly the projection itself, the updated positions of the MLC leaves and jaws may be fitted to the deformed projection of the tracking volumes in some manner, such as fitting the mid-position of the leaf to the outline of the object in the deformed portion and/or taking the leaf/jaw-to-projection-outline distance of the reference plan into account when setting the new positions. For example, the radiotherapy device parameter adaptation processing 140 may obtain treatment plan parameters for the identified segment that specify a distance between the leaf and/or jaw projection (e.g., a distance between an edge of the radiation beam to the OAR or a portion of the OAR). The radiotherapy device parameter adaptation processing 140 recomputes the segment to generate a new beam shape for the deformed portion that includes the portion of the OAR in a new position relative to the OAR position that is in the treatment plan parameters for the segment. When generating the new beam shape, the radiotherapy device parameter adaptation processing 140 may maintain the same specified distance between an edge of the radiation beam and the portion of the OAR in the new position as the distance in the treatment plan.

In an embodiment, the positions of the jaws and leaves of the MLC are adjusted to the outline of the projection contour, ensuring target (tumour) coverage. If the OARs have been included when creating the tracking volume for a given segment, the radiotherapy device parameter adaptation processing 140 may generate new segment parameters or control points that ensure that the OAR dose objectives specified in the treatment plan are not violated when setting the new leaf positions, by penalizing exposure of voxels belonging to OARs. For example, the radiotherapy device parameter adaptation processing 140 may reduce the size or shape of the beam for the segment in a way that decreases the amount of radiation exposure of the OARs.

As an example, the radiotherapy device parameter adaptation processing 140 optimizes MLC leaf positions based on the deformed identified portion(s). Specifically, the positioning of the leaves and jaws can be determined algorithmically by some criteria, such as maximum or mean position of the target position outline that is depicted in the deformed image portions. A slightly more sophisticated way is by optimization to include trade-offs between different objectives and/or using a machine learning model to decide the leaf position. An example of an optimization procedure for leaf positioning is provided below, where the ETV and the complementary ETV are used as tracking volumes. The function that is minimized (assuming radiotherapy device parameter adaptation processing 140 only penalizes underdose of the ETV and overdose of the complementary ETV) is defined as: $\min -w_1 n_{ETV,j} + w_2 n_{cETV,j}$, $n_{ETV,j}$, $n_{cETV,j} \geq 0$. The weights that fulfil $\Sigma_{i=1}^{2} w_i = 1$. $n_{ETV,j}$, $n_{cETV,j}$ are the number of voxels belonging to the ETV and the complementary ETV within the leaf pair j in the new segment. The number of voxels within each leaf pair j are determined by:

$$n_j = \int_{a_j}^{b_j} \rho_j(x) dx,$$

where $\rho_j(x)$ is the density of a given tracking volume along the axis parallel to the leaves and $a_j$ and $b_j$ are the positions of the leaves, such as the quantities that should be determined in the optimization. In an implementation, this optimization is inherently non-convex and can be only approximately solved.

In an increasingly advanced scenario, accumulated dose can be included in the positioning of the MLC leaves and jaws, yielding dosimetric tracking instead of or in addition to geometric tracking. The optimization above can then be updated to include the dose and dose density that will be delivered in the segment instead of or in addition to voxels and voxel density. In an embodiment, previously delivered dose to all structures can be considered when updating the current segment parameters. If the patient deformations are large, radiotherapy device parameter adaptation processing 140 can split the ETV in two or more parts after deformation. If dose is accumulated, this information can be used to construct new segments to compensate the lack of dose during or after treatment. And conversely, if some regions have received more dose than planned, segments or parts of segments can be removed during treatment to compensate for this effect.

In some embodiments, a first portion of the patient images in the treatment plan corresponds to a volumetric portion that is within a region to be irradiated during a first segment of a treatment fraction. For example, the treatment processing logic 120 identifies a first portion of the volume representation from the stack of 2D or 3D reference images of the patient that includes a target to be irradiated (e.g., a target within the beam's eye view) during the first segment of the treatment fraction (e.g., the first portion may only include the target and may exclude other regions that are also within the beam's eye view during the second segment). A second portion of the patient images is identified that includes a volumetric portion that is outside of the region to be irradiated. The second portion may be from the same beam delivery segment and/or from another, different beam delivery segment. For example, the treatment processing logic 120 identifies a second portion of the volume representation based on the 2D or 3D reference images of the patient that does not include the target to be irradiated (e.g., a target within the beam's eye view) but includes an OAR that is outside of the beam's eye view (e.g., an OAR that is visible by the beam or is within view of the collimator during a subsequent or previous segment and/or an OAR that is not visible by the beam during the first segment). For example, the treatment processing logic 120 identifies a second portion of the 2D or 3D reference images of the patient that includes a portion of the target to be irradiated (e.g., a target within the beam's eye view) that is outside of the beam's eye view during the first segment but is within the beam's eye view during a second segment. The first and second portions are deformed separately based on the patient deformation model. After the first and second portions are deformed, the radiotherapy device parameter adaptation processing 140 updates the beam delivery segment(s) (e.g., parameters of the current, previous, and/or subsequent segments) based on the deformed versions of the first and second portions.

In some embodiments, a first portion of the patient images in the treatment plan corresponds to a volumetric portion that is within a region that includes a target to be irradiated during a first segment of a treatment fraction. For example, the treatment processing logic 120 identifies a first portion of the volume representation of the 2D or 3D reference images of the patient that includes a target to be irradiated (e.g., a target within the beam's eye view) during the first segment of the treatment fraction (e.g., the first portion may only include the target and may exclude other regions that are also within the beam's eye view during the second segment). A second portion of the patient images is identified that includes a volumetric portion of the target irradiated during a second segment (the second segment is adjacent to or non-adjacent to the first segment). For example, the treatment processing logic 120 identifies a second portion of the volume representation of the 2D or 3D reference images of the patient that includes the target to be irradiated (e.g., a target within the beam's eye view) during the second segment of the treatment fraction (e.g., the second portion may only include the target and may exclude other regions that are also within the beam's eye view during the second segment). The first and second portions are deformed separately based on the patient deformation model. After the first and second portions are deformed, the radiotherapy device parameter adaptation processing 140 updates the beam delivery segment(s) (e.g., parameters of the current, previous, and/or subsequent segments) based on the deformed versions of the first and second portions.

Figure 4:
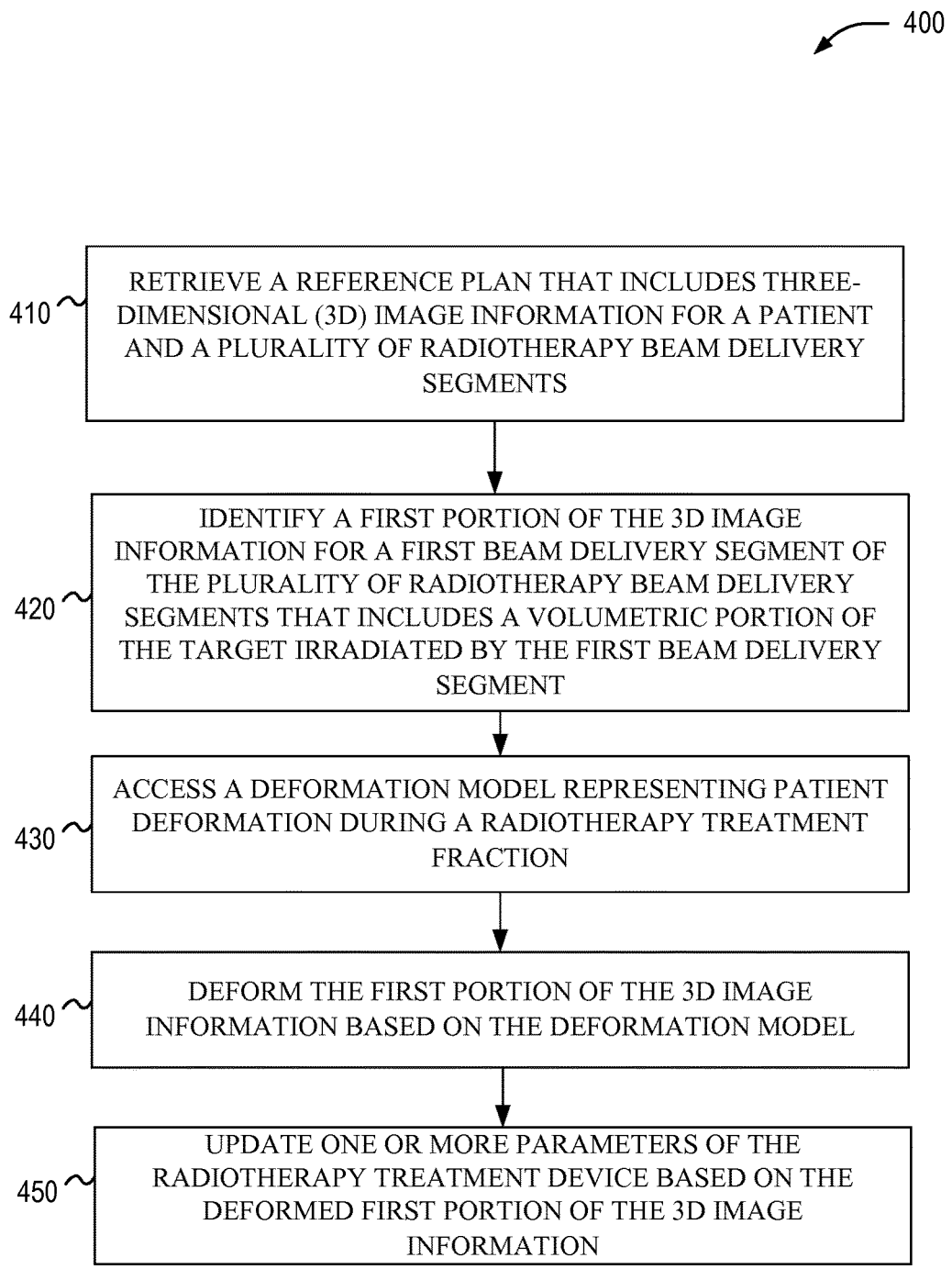
FIGS. 4 and 5 illustrate flowcharts of exemplary operations for performing geometry-based radiotherapy treatment according to some examples of the disclosure.

FIG. 4 is a flowchart illustrating example operations of the treatment processing logic 120 in performing process 400, according to example embodiments. The process 400 may be embodied in computer-readable instructions for execution by one or more processors such that the operations of the process 400 may be performed in part or in whole by the functional components of the treatment processing logic 120; accordingly, the process 400 is described below by way of example with reference thereto. However, in other embodiments, at least some of the operations of the process 400 may be deployed on various other hardware configurations. The process 400 is therefore not intended to be limited to the treatment processing logic 120 and can be implemented in whole, or in part, by any other component. Some or all of the operations of process 400 can be in parallel, out of order, or entirely omitted.

At operation 410, treatment processing logic 120 retrieves a reference plan that includes three-dimensional (3D) volume representation based on image information for a patient and a plurality of radiotherapy beam delivery segments.

At operation 420, treatment processing logic 120 identifies a first portion of the 3D image information for a first beam delivery segment of the plurality of radiotherapy beam delivery segments that includes a volumetric portion of the target irradiated by the first beam delivery segment.

At operation 430, treatment processing logic 120 accesses a deformation model representing patient movement during a radiotherapy treatment fraction.

At operation 440, treatment processing logic 120 deforms the first portion of the 3D image information based on the deformation model.

At operation 450, treatment processing logic 120 updates one or more parameters of the radiotherapy treatment device based on the deformed first portion of the 3D image information.

Figure 5:
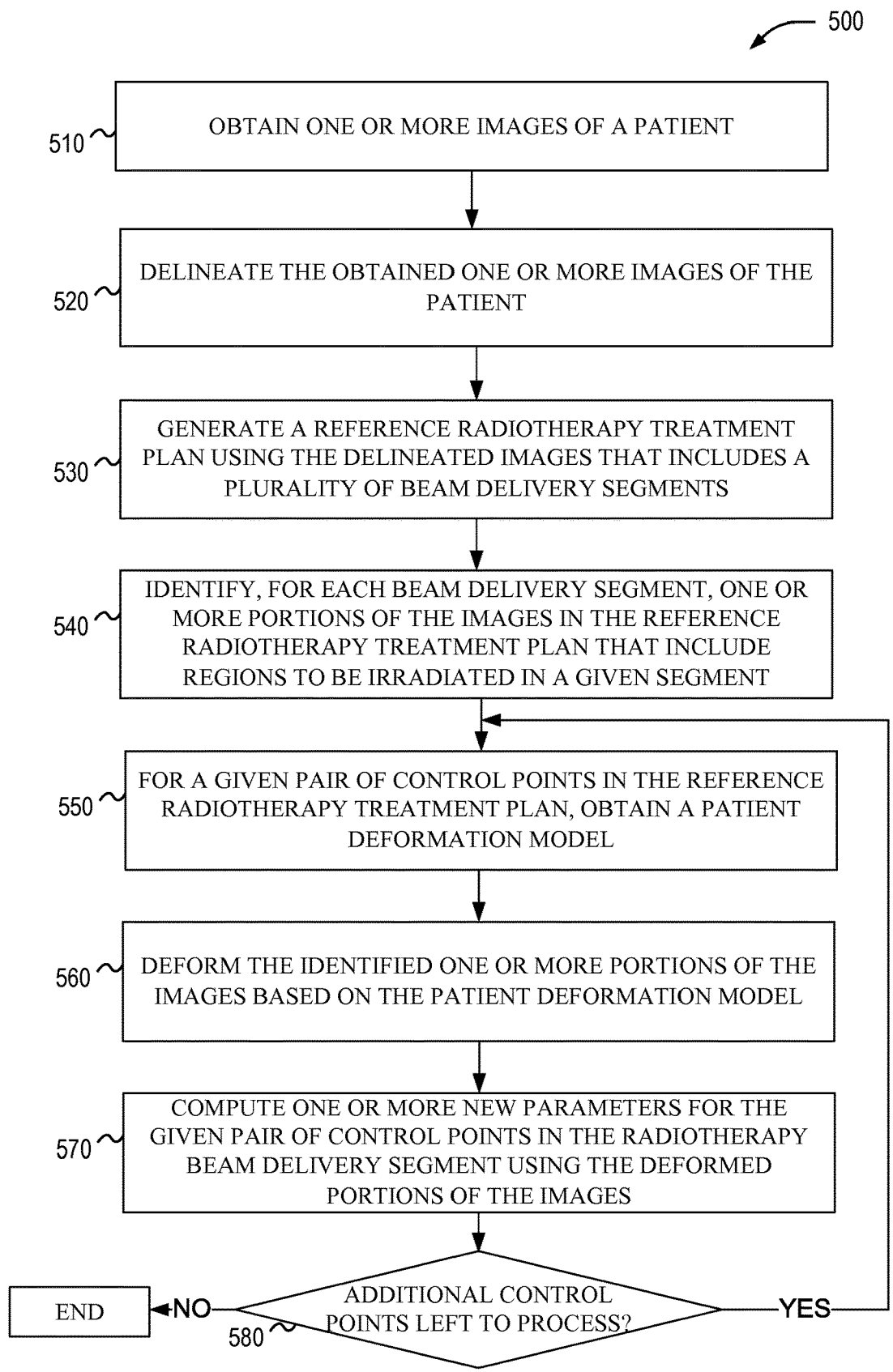

FIG. 5 is a flowchart illustrating example operations of the treatment processing logic 120 in performing process 500, according to example embodiments. The process 500 may be embodied in computer-readable instructions for execution by one or more processors such that the operations of the process 500 may be performed in part or in whole by the functional components of the treatment processing logic 120; accordingly, the process 500 is described below by way of example with reference thereto. However, in other embodiments, at least some of the operations of the process 500 may be deployed on various other hardware configurations. The process 500 is therefore not intended to be limited to the treatment processing logic 120 and can be implemented in whole, or in part, by any other component. Some or all of the operations of process 500 can be in parallel, out of order, or entirely omitted.

At operation 510, treatment processing logic 120 obtains one or more images of a patient.

At operation 520, treatment processing logic 120 delineates the obtained one or more images of the patient.

At operation 530, treatment processing logic 120 generates a reference radiotherapy treatment plan using the delineated images that includes a plurality of beam delivery segments.

At operation 540, treatment processing logic 120 identifies, for each beam delivery segment, one or more portions of the images in the reference radiotherapy treatment plan that include regions to be irradiated in a given segment.

At operation 550, treatment processing logic 120, for a given pair of control points in the reference radiotherapy treatment plan, obtains a patient deformation model.

At operation 560, treatment processing logic 120 deforms the identified one or more portions of the images based on the patient deformation model.

At operation 570, treatment processing logic 120 computes one or more new parameters for the given pair of control points in the radiotherapy beam delivery segment using the deformed portions of the images.

At operation 580, treatment processing logic 120 determines if additional control points remain to be processed and if so, proceeds to operation 550 to compute new parameters by deforming portions of images for the additional control points.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 202, perform or implement the operations of the processes 400 and 500, or perform any one or more of the other methodologies discussed herein. In various embodiments, such electronic computing systems or devices operate as standalone devices or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present inventive subject matter, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the inventive subject matter can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the inventive subject matter or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present inventive subject matter also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the inventive subject matter.

In view of the above, it will be seen that the several objects of the inventive subject matter are achieved and other beneficial results attained. Having described aspects of the inventive subject matter in detail, it will be apparent that modifications and variations are possible without departing from the scope of aspects of the inventive subject matter as defined in the appended claims. As various changes could be made in the above constructions, products, and methods without departing from the scope of aspects of the inventive subject matter, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the present disclosure without departing from its scope. While the dimensions, types of materials and example parameters, functions, and implementations described herein are intended to define the parameters of the inventive subject matter, they are by no means limiting and are exemplary embodiments. Many other embodiments will be apparent to those of skill in the art upon reviewing the above description. The scope of the inventive subject matter should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the inventive subject matter should be determined with reference to the appended claims, along with the full scope of equivalents to which such claims are entitled.

What is claimed is:

1. A method for adjusting radiotherapy treatment for a patient in real time, the method comprising:
   retrieving, by processor circuitry, a reference plan that includes three-dimensional (3D) volume representation of information for the patient and a plurality of radiotherapy beam delivery segments;
   identifying, by the processor circuitry, a first portion of the 3D volume representation of information for a first beam delivery segment of the plurality of radiotherapy beam delivery segments that includes a volumetric portion of a target to be irradiated by the first beam delivery segment;
   for the same first beam delivery segment, identifying, within the first portion of the 3D volume representation of information, a first 3D volumetric region and a second 3D volumetric region, the first 3D volumetric region being drawn from the 3D volume representation of information to include only a portion of the target, the second 3D volumetric region being drawn from the 3D volume representation of information to include only a portion of an organ at risk (OAR);
   accessing, by the processor circuitry, a deformation model representing patient deformation during a radiotherapy treatment fraction;
   deforming, by the processor circuitry, each of the first and second 3D volumetric regions corresponding to the first beam delivery segment separately and independently from each other based on the deformation model; and
   updating, by the processor circuitry, one or more parameters of a radiotherapy treatment device based on the deformed first and second 3D volumetric regions.

2. The method of claim 1, wherein the reference plan includes delineations of one or more of target volumes and/or one or more organs-at-risk (OARs), and wherein the 3D volume representation of information includes a plurality of two-dimensional image slices of the patient or a 3D volumetric representation of the patient.

3. The method of claim 1, further comprising generating the deformation model based on a description of the patient captured prior to or during the radiotherapy treatment fraction, the description being based on one or more image capture modalities.

4. The method of claim 1 further comprising:
tracing a path, associated with the first beam delivery segment, from an imaginary eye of a multi-leaf collimator (MLC) through a set of pixels in a virtual screen;
calculating a color of an object visible through the virtual screen;
generating a first 3D cut-out of the patient based on the color of the object representing a projection image of a beam's eye view from the MLC of an anatomy depicted in the 3D volume representation;
identifying the first portion based on the first 3D cut-out of the patient; and
generating an elementary tracking volume (ETV) for the first beam delivery segment by intersecting a 3D target volume of the target and the first 3D cut-out of the patient.

5. The method of claim 4 further comprising:
generating a second 3D cut-out of the patient by projecting an opening of the collimator at a second of the plurality of radiotherapy beam delivery segments with respect to a source position; and
identifying a second portion of the 3D volume representation of information for the second radiotherapy beam delivery segment based on the second 3D cut-out of the patient.

6. The method of claim 1, wherein the volumetric portion in the first portion includes a part of the target to be irradiated and an OAR, further comprising:
identifying a first set of voxels in the first portion that corresponds to the target to be irradiated;
identifying a second set of voxels in the first portion that corresponds to the OAR;
deforming the first set of voxels separately from deforming the second set of voxels based on the deformation model; and
changing a shape of the beam delivered during the first radiotherapy beam delivery segment based on the deformed first and second sets of voxels.

7. The method of claim 1 further comprising identifying a second portion of the 3D volume representation of information that includes a volumetric portion that is outside of a region that is irradiated in the first beam delivery segment.

8. The method of claim 7 further comprising:
deforming the first and second portions separately based on the deformation model; and
updating the one or more parameters of the radiotherapy treatment device based on the deformed first and second portions.

9. The method of claim 1, wherein deforming the first portion comprises applying a geometrical transform defined by the deformation model to the first portion.

10. The method of claim 1, wherein the one or more parameters of the radiotherapy treatment device are updated based on treatment objectives defined by the reference plan, wherein at least one of the treatment objectives penalizes exposure of voxels belonging to an organ-at-risk (OAR) preventing adjustment of the one or more parameters that result in increased dose to the OAR.

11. The method of claim 1, wherein updating the one or more parameters comprises adjusting positions of multi-leaf collimator leaves and jaws to fit an outline of an object depicted in the volumetric portion.

12. The method of claim 1 further comprising:
identifying a second portion of the 3D volume representation of information for a second of the plurality of radiotherapy beam delivery segments that includes a second volumetric portion of the target irradiated by the second beam delivery segment;
deforming the second portion of the 3D volume representation of information based on the deformation model; and
updating one or more parameters of the radiotherapy treatment device based on the deformed second portion of the 3D volume representation of information.

13. The method of claim 12 further comprising combining the first portion and the second portions into a combined portion of the 3D volume representation of information, wherein the deforming and updating is performed for the combined portion of the 3D volume representation of information.

14. A non-transitory computer-readable medium comprising computer-readable instructions for adjusting radiotherapy treatment for a patient in real time, the computer-readable instructions comprising instructions for performing operations comprising:
retrieving a reference plan that includes three-dimensional (3D) volume representation of information for the patient and a plurality of radiotherapy beam delivery segments;
identifying a first portion of the 3D volume representation of information for a first beam delivery segment of the plurality of radiotherapy beam delivery segments that includes a volumetric portion of a target to be irradiated by the first beam delivery segment;
for the same first beam delivery segment, identifying, within the first portion of the 3D volume representation of information, a first 3D volumetric region and a second 3D volumetric region, the first 3D volumetric region being drawn from the 3D volume representation of information to include only a portion of the target, the second 3D volumetric region being drawn from the 3D volume representation of information to include only a portion of an organ at risk (OAR);
accessing a deformation model representing patient deformation during a radiotherapy treatment fraction;
deforming each of the first and second 3D volumetric regions corresponding to the first beam delivery segment separately and independently from each other the first portion of the 3D-volume representation of information based on the deformation model; and
updating one or more parameters of a radiotherapy treatment device based on the deformed first and second 3D volumetric regions first-portion of the-3D-volume representation of information.

15. The non-transitory computer-readable medium of claim 14, wherein the reference plan includes delineations of one or more of target volumes and/or one or more organs-at-risk (OARs), and wherein the 3D volume representation of information includes a plurality of two-dimensional image slices of the patient or a 3D volumetric representation of the patient.

16. The non-transitory computer-readable medium of claim 14, wherein the operations further comprise generating the deformation model based on a description of the patient captured prior to or during the radiotherapy treatment fraction, the description being based on one or more image capture modalities.

17. The non-transitory computer-readable medium of claim 14, wherein the operations further comprise:
  generating a first 3D cut-out of the patient by projecting an opening of a collimator at the first beam delivery segment with respect to a source position; and
  identifying the first portion based on the first 3D cut-out of the patient.

18. A system for adjusting radiotherapy treatment for a patient in real time, the system comprising:
  one or more processors for performing operations comprising:
  retrieving a reference plan that includes three-dimensional (3D) volume representation of information for the patient and a plurality of radiotherapy beam delivery segments;
  identifying a first portion of the 3D volume representation of information for a first beam delivery segment of the plurality of radiotherapy beam delivery segments that includes a volumetric portion of a target to be irradiated by the first beam delivery segment;
  for the same first beam delivery segment, identifying, within the first portion of the 3D volume representation of information, a first 3D volumetric region and a second 3D volumetric region, the first 3D volumetric region being drawn from the 3D volume representation of information to include only a portion of the target, the second 3D volumetric region being drawn from the 3D volume representation of information to include only a portion of an organ at risk (OAR);
  accessing a deformation model representing patient deformation during a radiotherapy treatment fraction,
  deforming each of the first and second 3D volumetric regions corresponding to the first beam delivery segment separately and independently from each other based on the deformation model; and
  updating one or more parameters of a radiotherapy treatment device based on the deformed first and second 3D volumetric regions first.

19. The system of claim 18, wherein the reference plan includes delincations of one or more of target volumes and/or one or more organs-at-risk (OARs), and wherein the 3D volume representation of information includes a plurality of two-dimensional image slices of the patient or a 3D volumetric representation of the patient.

20. The system of claim 18, wherein the operations further comprise generating the deformation model based on a description of the patient captured prior to or during the radiotherapy treatment fraction, the description being based on one or more image capture modalities.

21. The system of claim 18, wherein the operations further comprise:
  generating a first 3D cut-out of the patient by projecting an opening of a collimator at the first beam delivery segment with respect to a source position; and
  identifying the first portion based on the first 3D cut-out of the patient.

* * * * *

UNITED STATES PATENT AND TRADEMARK OFFICE
CERTIFICATE OF CORRECTION

PATENT NO. : 12,251,577 B2
APPLICATION NO. : 17/594432
DATED : March 18, 2025
INVENTOR(S) : Riad et al.

Page 1 of 1

It is certified that error appears in the above-identified patent and that said Letters Patent is hereby corrected as shown below:

In the Claims

In Column 24, Line 65, in Claim 2, delete "delincations" and insert --delineations-- therefor In Column 26, Lines 48-50, in Claim 14, after "other", delete "the first portion of the 3D-volume representation of information"

In Column 26, Line 53-54, in Claim 14, delete "regions first-portion of the-3D-volume representation of information." and insert --regions.-- therefor In Column 28, Line 2, in Claim 18, delete "fraction," and insert --fraction;-- therefor In Column 28, Line 9, in Claim 18, delete "regions first." and insert --regions.-- therefor In Column 28, Line 11, in Claim 19, delete "delincations" and insert --delineations-- therefor Signed and Sealed this
Thirtieth Day of September, 2025

John A. Squires
*Director of the United States Patent and Trademark Office*